US005147686A

United States Patent [19]

Ichimura et al.

[11] Patent Number: 5,147,686

[45] Date of Patent: Sep. 15, 1992

[54] METHOD OF MAKING TITANIUM OXIDE POWDER HAVING ANTIMICROBIAL METAL SUPPORTED THEREON

[75] Inventors: Kenichi Ichimura, Moriyama; Hajime Murakami; Nobutoshi Yamada, Otsu; Sadanori Mizukoshi, Moriyama, all of Japan

[73] Assignee: Ishihara Sangyo Kaisha, Ltd., Osaka, Japan

[21] Appl. No.: 639,183

[22] Filed: Jan. 9, 1991

Related U.S. Application Data

[62] Division of Ser. No. 323,874, Mar. 15, 1989, abandoned.

[30] Foreign Application Priority Data

Mar. 17, 1988 [JP] Japan ..... 63-64392
Mar. 17, 1988 [JP] Japan ..... 63-64393

[51] Int. Cl.$^5$ ..... B05D 7/24

[52] U.S. Cl. ..... 427/217; 427/180; 427/242; 424/421; 424/630; 424/641; 106/18.36; 106/436; 106/440

[58] Field of Search ..... 427/217, 242, 180, 250, 427/252, 251; 424/489, 490, 630, 641, 642, 421; 106/18.36, 286.6, 286.7, 440, 436; 423/604, 610, 622; 118/716; 241/101 D

[56] References Cited

U.S. PATENT DOCUMENTS

| | | | |
|---|---|---|---|
| 2,232,723 | 2/1941 | Patterson | 106/440 |
| 2,476,372 | 7/1949 | Heiks | 106/18.36 |
| 3,549,357 | 12/1970 | Osborne | 427/242 |
| 3,598,627 | 8/1971 | Klimboff | 106/18.36 |
| 3,884,706 | 5/1975 | Little | 106/18.36 |
| 3,888,176 | 6/1975 | Horai, Jr. et al. | 106/18.36 |
| 3,888,682 | 6/1975 | Nelson | 106/18.36 |
| 3,888,683 | 6/1975 | Horai, Jr. et al. | 106/18.36 |
| 3,956,007 | 5/1976 | Modly | 106/440 |
| 4,092,441 | 5/1978 | Meyer et al. | 106/18.36 |
| 4,243,728 | 1/1981 | Sato et al. | 427/217 |
| 4,775,585 | 10/1988 | Hagiwara et al. | 428/403 |
| 4,849,223 | 7/1989 | Pratt et al. | 424/78 |
| 4,906,466 | 3/1990 | Edwards et al. | 424/78 |
| 4,915,987 | 4/1990 | Nara et al. | 427/242 |

FOREIGN PATENT DOCUMENTS

| | | | |
|---|---|---|---|
| 1295958 | 5/1969 | Fed. Rep. of Germany | 427/250 |
| 51-75732 | 6/1976 | Japan | 106/18.36 |
| 58-150424 | 9/1983 | Japan | 427/217 |
| 62-112704 | 5/1987 | Japan | 427/217 |
| 1041554 | 9/1983 | U.S.S.R. | 106/440 |

*Primary Examiner*—Michael Lusignan
*Assistant Examiner*—Terry J. Owens
*Attorney, Agent, or Firm*—Cushman, Darby & Cushman

[57] ABSTRACT

Antimicrobial powders are obtained by suppporting at least one antimicrobial metal of copper, zinc and alloys thereof on the surface of hydrous titanium oxide or titanium oxide particles by electroless plating, vapor deposition, compression mixing, mixing and reducing, and thermal decomposition of a compound. These powders are used to provide antimicrobial resin compositions, antimicrobial rubber compositions, antimicrobial glass compositions and antimicrobial coating compositions.

1 Claim, No Drawings

METHOD OF MAKING TITANIUM OXIDE POWDER HAVING ANTIMICROBIAL METAL SUPPORTED THEREON

This application is a division of Ser. No. 323,874, filed Mar. 15, 1989, now abandoned.

BACKGROUND OF THE INVENTION

1. Field of the Invention

The present invention relates to antimicrobial powders which comprise an antimicrobial metal supported on the surface of hydrous titanium oxide or titanium oxide particles and a method for making them.

2. Description of the Related Art

It is well known that metals such as copper and silver have antimicrobial properties as so-called oligodynamic action. For example, there have been proposed uses of such metals in therapeutic or preventive medicines which use copper ion generated from various soluble copper salts, copper complex compounds, etc.. Uses of such metals are also made in bactericidal filters, algicidal filter, algicidal net, bactericidal and deodorant cloths or leathers employing superfine copper fibers produced from copper metal. Specifically, Japanese Patent Kokai No. 88109/88 discloses an antibacterial composition comprising a support of an oxide of Ti, Mg, Al or the like on which silver chloride is applied.

Recently, materials, industrial products and constructions have suffered from various damages by microorganisms such as molds and bacteria and other harmful organisms and many proposals have been made in an attempt to prevent such damages. One of them is the use of the above metallic copper fibers and besides various preventive means using antimicrobial properties of the above-mentioned metals have been extensively studied. For example, it has been attempted to support a metal component on solid powders such as zeolite by ion exchange reaction. (cf. Japanese Patent Kokai No. 133235/84).

However, the aforementioned silver chloride-supporting oxides and metal component-supporting zeolite powders have the following defects. That is, it is difficult to make them in the form of fine particles. The supported metal component readily falls off from the surface of particles. They are not sufficiently dispersible in media such as paint coating compositions, resin moldings, resin films, and coating compositions for paper processing. The amount must be increased in order to obtain sufficient antimicrobial effect and as a result, color tone of coated articles or molded articles applied therewith is damaged and desired color cannot be obtained. Thus, improvements thereof has been demanded. In case of appliances and high-grade household furnitures subjected to antimicrobial treatment which require beautiful coloring, the above improvement has been especially strongly desired.

SUMMARY OF THE INVENTION

The object of the present invention is to provide antimicrobial powders which are free from the above problems and which have superior antimicrobial properties and furthermore, to provide an antimicrobial composition excellent in color tone by adding or applying the antimicrobial powders to various media.

DETAILED DESCRIPTION OF THE PREFERRED EMBODIMENTS

The inventors have made various studies on the added value of hydrous titanium oxide or titanium oxide powders as the functional material or on making composite materials from the hydrous titanium oxide or titanium oxide. In the course of the study, they have recognized the application of antimicrobial powders as a substrate and have made further studies to find that these titanium oxide powders are conspicuously superior in adhesion of antimicrobial metal components to the surface thereof and hence retention of the antimicrobial effect can be prolonged and besides coloring property of compositions comprising titanium oxide powders on which antimicrobial metal is supported can be further improved. The present invention has been accomplished based on this finding. That is, the present invention resides in antimicrobial powders, characterized by comprising at least one antimicrobial metal selected from the group consisting of copper, zinc and alloys thereof which is supported on the surface of hydrous titanium oxide or titanium oxide.

The hydrous titanium oxide or titanium oxide (hereinafter referred to as "substrate particles") which supports the antimicrobial metal component in the present invention includes, in addition to so-called hydrous titanium dioxide represented by $TiO_2.nH_2O$, various hydrated titanium dioxides, ordinary titanium dioxide having Ti:O of nearly 1:2, so-called lower titanium oxide having various Ti:O, titanium-nickel-antimony system and titanium-chromium-antimony mainly composed of titanium dioxide as constituting component, and various titanium oxide composite pigments and synthetic rutile pigments. These substrate particles have an average particle size of normally 0.01–3 μm, desirably 0.02–1 μm and more desirably 0.03–0.4 μm. These substrate particles may be those which are produced by various methods such as, for example, (1) titanium dioxide powders obtained by vapor phase oxidation decomposition of titanium tetrachloride, (2) hydrous titanium dioxide obtained by hydrolysis of a titanium sulfate solution, titanium tetrachloride solution or organotitanium compound solution, if necessary, in the presence of a nucleating seed, (3) titanium dioxide powders obtained by calcining hydrous titanium dioxide, (4) various lower titanium oxide powders obtained by subjecting to thermal reduction treatment the hydrous titanium dioxide precipitate or titanium dioxide powders obtained in the above (1), (2) or (3), and (5) titanium oxide composite pigments obtained by adding a coloring metal component to the hydrous titanium oxide precipitate obtained in the above (2), followed by reaction with heating.

The antimicrobial metal supported on the substrate particles in the present invention includes metallic copper, metallic zinc, and copper and/or zinc-based alloys such as a Cu-Zn alloy, Cu-Ag alloy, Cu-Sn alloy, Cu-Al alloy, Zn-Sn alloy, Zn-Sn-Cu alloy, Zn-Al-Cu-Mg alloy and the like. These metals may be supported alone or in combination of two or more. The amount of the metal component supported is normally 0.001–35%, preferably 0.01–30% in terms of metal based on the weight of substrate particles. If the amount is less than the above range, the desired antimicrobial effect cannot be exhibited and if more than the range, not only is this disadvantageous for cost, but also the dispersibility in the medium to be imparted with the antimicrobial property and coloring property are sometimes damaged. Supporting the antimicrobial metal on the substrate particles in the present invention can be performed by various methods such as: (1) so-called electroless plating method according to which a plating bath is prepared by adding a reducing agent and, if necessary, a buffer, a complexing agent and a pH modifier to an aqueous solution of metal ion which contains the antimicrobial metal component and immersing the substrate particles in this plating bath, followed by stirring for a given period to deposit the metal ion as metal film on the surface of the particles and in this case, if the substrate particles are previously immersed in an aqueous solution of, for example, palladium or tin, to deposit the metal on the surface of the particles before the deposition of the film of the antimicrobial metal, (deposition of film of the antimicrobial metal component can be further efficiently attained and besides a firm film of good adhesion can readily be formed,) (2) a method which comprises heating and dissolving the antimicrobial metal in a vacuum deposition apparatus to vapor deposit the metal on the surface of the substrate particles; (3) a method which comprises thermally decomposing various organic compounds such as alkyl metal compounds and organometal complex compounds containing the antimicrobial metal component on the substrate particles to support the metal on the surface of the particles; (4) a method according to which the substrate particles and the antimicrobial metal powders are charged in a dry- or wet-type compressing grinder such as a ball mill or edge runner mill and are compression mixed therein to support the antimicrobial metal on the surface of the substrate particles; and (5) a method according to which an antimicrobial metal compound is added to the aforementioned hydrous titanium dioxide to support the antimicrobial metal component on the surface of the hydrous titanium dioxide particles and then this is heated in a reducing gas atmosphere to support the antimicrobial metal on the surface of titanium oxide particles. Among these methods, especially those of (1) and (2) can provide firm adhesion of antimicrobial metal onto the surface of substrate particles and thus can further enhance developability and retentivity of the antimicrobial effect. When the supporting methods of (1), (3) and (4) are conducted, it is desired to carry them out in an inert gas atmosphere such as nitrogen gas so as to prevent oxidation as far as possible.

The antimicrobial powders of the present invention are useful against various microorganisms. As these microorganisms, mention may be made of, for example, Gram-positive bacteria (such as *Bacillus subtilis, Staphylococcus aureus,* and *Streptococcus pyogenes*), Gram-negative bacteria (such as *Escherichia coli, Salmonella typhimurium, Klebsiella pneumoniae, Serratia marcescens, Proteus morganii, Proteus Vulgaris, Pseudomonas aeruginosa,* and *Vibrio parahaemolyticus*), trichophyton (such as *Trichophyton mentagraphytes* and *Trichophyton rubrum*), eumycetes (such as *Candida albicans*), molds (such as *Penicillium chrysogenum, Penicillium citrinum, Cladosporium fulvum, Aspergillus fumigatus, Aspergillus niger* and *Cladosporium herbarum*).

The resulting antimicrobial powders can be added to various resins, rubbers, glasses, etc. to produce antimicrobial compositions or can be used for antimicrobial treatment of industrial and household electrical equipment, furnitures, furnishing materials, packaging materials for foods by various methods known per se or can be utilized as antimicrobial agents for various environmental health facilities or equipment.

In the antimicrobial powders obtained by the present invention, the antimicrobaal metal component is firmly supported on the surface of substrate particles and increase of retentivity of antimicrobial effect can be further expected. Besides, they have excellent optical characteristics such as high hiding power inherent to the titanium dioxide of the substrate particles and furthermore good dispersibility and are high in industrial value as antimicrobial property imparting materials and coloring materials in a wide variety of fields.

The present invention will be explained further be the following examples and comparative examples.

EXAMPLE 1

10 Grams of titanium dioxide particles (rutile type titanium dioxide obtained by vapor phase oxidation decomposition of titanium tetrachloride and having the composition as shown in Table 1) as substrate particles were immersed in 20% hydrofluoric acid with stirring for 60 minutes, followed by filtration, washing with water and drying. Then, 5 g of the product was first immersed in 1 liter of an aqueous stannous chloride solution (0.5 g/1) and then immersed in 1 liter of an aqueous palladium chloride solution (0.5 g/1) to deposit palladium on the surface of titanium dioxide particles. The thus pretreated titanium dioxide was introduced into 500 ml of a plating bath (copper sulfate: 70 g/1, Rochelle salt: 350 g/1 and sodium hydroxide: 100 g/1) and with gentle stirring when the bath temperature reached 25° C., thereto and added 100 ml of 37% formalin solution was gradually added. After completion of the addition, stirring was further continued at the same temperature for 90 minutes to deposit a film of metallic copper on the surface of the substrate particles by electroless plating. Thereafter, titanium dioxide particles were collected by filtration, washed with water and dried to obtain the objective antimicrobial powders.

TABLE 1

| Crystal form | | Rutile |
|---|---|---|
| Particle size (μm) | | 0.2~0.4 |
| True specific gravity | | 4.2 |
| Bulk specific gravity (gr/cm$^3$) | | 0.5~0.7 |
| Oil absorption | | 12~14 |
| Analysis | $TiO_2$ (%) | 99.8 |
| | $Al_2O_3$ (%) | 0.002 |
| | $SiO_2$ (%) | 0.02 |
| | $Fe_2O_3$ (%) | 0.0034 |
| | $P_2O_3$ (%) | 0.000 |
| | $Na_2O$ (%) | 0.005 |
| | $Nb_2O_3$ (%) | 0.00 |
| | $SO_3$ (%) | 0.00 |
| | $H_2O$ (%) | 0.04 |
| | Igloss (%) | 0.09 |

EXAMPLE 2

70 grams of rutile-type titanium dioxide particles having the composition as shown in Table 1 were suspended in 500 ml of 3% hydrofluoric acid and stirred for about 30 minutes under normal pressure, followed by filtration, washing with water drying and grinding. A solution was separately prepared by adding 0.1 g of silver nitrate to 1 liter of water and adding ammonia water until the resulting precipitate was redissolved. 50grams of the above ground product was introduced into this solution and dispersed with stirring for about 60 minutes. Then, to the dispersion was gradually added 30 ml of a previously prepared reducing solution (glucose: 45 g, tartaric acid: 4 g, alcohol: 100 ml, water: 1 liter), followed by filtration and washing until specific filtration resistance reached 125 μs or less and then drying and grinding. This ground product was introduced into 5 liter of a plating bath (copper sulfate: 70 g/1, Rochelle salt: 350 g/1 and sodium hydroxide: 10 g/1) and under gentle stirring when the bath temperature reached 50° C., thereto was gradually added 1 liter of 37% formalin solution to deposit a film of metallic copper on the surface of titanium dioxide particles, followed by filtration, washing and drying to obtain the objective antimicrobial powders.

EXAMPLE 3

240 grams of the rutile-type titanium dioxide powders as shown in Table (1 used as substrate particles) were suspended in water to obtain an aqueous concentrated slurry (237 g/1 of solid content). A 250 ml portion of this slurry was taken and thereinto was introduced 10 g of brass powders (Cu+Zn alloy; BRA-AT-200 manufactured by Fukuda Kinzoku Haku Kogyo Co.) and this was well mixed by a Henschel mixer. Thereafter, the mixture was subjected to compression mixing for 24 hours in a magnetic ball mill (internal volume of the mill was 1 liter; filled with 500 ml of alumina balls of 10 mm in diameter; amount of slurry was 250 ml and number of revolution was 100 rpm) to support the brass alloy on the surface of the substrate particles. After completion of the ball mill treatment, the slurry was taken out and diluted and repeatedly subjected to sedimentation separating to fractionate the titanium dioxide particles from the brass particles. The titanium dioxide slurry after completion of the fractionation was subjected to filtration, washing with water and drying to obtain the objective antimicrobial powders.

EXAMPLE 4

The procedure of Example 3 was repeated except that 10 g of copper particles (CU-AT-200 manufactured by Fukuda Kinzoku Haku Kogyo Co.) were introduced into 250 ml of the concentrated aqueous slurry of substrate particles used in Example 3 to obtain the objective antimicrobial powders comprising metallic copper supported on the surface of substrate particles.

EXAMPLE 5

200 grams of rutile type titanium dioxide powders having the composition as shown in Table 1 were suspended in 300 ml of water to make a slurry. Then, to this slurry was added a solution prepared by dissolving 22 g of cupric chloride in 100 ml of water. Then, this was neutralized by gradually adding 0.5N sodium hydroxide solution with stirring so that pH of the slurry reached 7–8, followed by aging. The resulting slurry was subjected to filtration, washing and drying to deposit copper hydroxide on the titanium dioxide particles. Then, 50 g of the titanium dioxide deposited with copper hydroxide was put in a stainless steel boat and calcined at 400° C. for 30 minutes in a tubular oven under nitrogen gas stream. Then, the nitrogen gas stream was replaced with hydrogen gas and the calcined titanium dioxide was reduced with heating at 400° C. for 4 hours under hydrogen gas stream. Thereafter, the product was cooled to room temperature in nitrogen gas stream and taken out from the oven to obtain the objective antimicrobial powders comprising metallic copper supported on the surface of titanium dioxide.

EXAMPLE 6

10 grams of rutile type titanium dioxide powders having the composition as shown in Table 1 were spread in a glass petri dish (diameter: 65 mm). This was placed in a vacuum deposition apparatus (HUS5GB manufactured by Hitachi Limited) and a brass piece was placed between electrodes. In this apparatus a given amount of brass was vapor deposited on the surface of the titanium dioxide particles to obtain the objective antimicrobial powders.

EXAMPLE 7

The procedure of Example 2 was repeated except that 70 g of hydrous titanium dioxide dry product prepared by the following method was used in place of rutile type titanium dioxide powders to obtain the objective antimicrobial powders.

500 milliliters of an aqueous titanium tetrachloride solution (207 g/1 in terms of $TiO_2$) was gently heated and when the temperature reached 75° C., thereto was immediately added 100 ml of a seed agent for acceleration of rutile crystallization (104 g/1 in terms of $TiO_2$) and the temperature of the solution was kept at 74°–76° C. with stirring to allow hydrolysis reaction to proceed for 200 minutes. When the temperature decreased to room temperature, the resulting slurry was repeatedly subjected to dilution decantation with water, followed by filtration, washing with water and drying to obtain a hydrous titanium dioxide dry product.

EXAMPLE 8

20 grams of rutile type titanium dioxide powders of the composition as shown in Table 1 were suspended in 400 ml of ethylene glycol and this suspension was charged in a four-necked flask provided with a stirrer and stirred for 30 minutes in a nonoxidizing atmosphere while introducing nitrogen gas. Then, thereto was added 6.7 g of $Cu(C_5H_7O_2)_2$, followed by stirring for further 15 minutes. Thereafter, the suspension was heated to 190° C. (at 4° C./min) and kept at this temperature for 60 minutes to effect thermal decomposition of $Cu(C_5H_7O_2)_2$. Then, the suspension was subjected to filtration and washing (with toluene) to obtain a cake. This cake was gently dried at a low temperature to obtain the objective antimicrobial powders comprising metallic copper supported on the particles.

EXAMPLE 9

The procedure of Example 8 was repeated except that 20 g of hydrous titanium dioxide dry product used in Example 7 was used in place of rutile type titanium dioxide powder, thereby to obtain the objective antimicrobial powders.

The powders having antimicrobial metal supported thereon obtained in Examples 1–9 were respectively put in containers, the atmosphere of which was replaced with nitrogen gas. Properties of these samples are shown in Table 2.

TABLE 2

| Property | Example 1 | 2 | 3 | 4 | 5 | 6 | 7 | 8 | 9 |
|---|---|---|---|---|---|---|---|---|---|
| Sample mark | $A_1$ | $A_2$ | $A_3$ | $A_4$ | $A_5$ | $A_6$ | $A_7$ | $A_8$ | $A_9$ |
| Average particle size (μm) | 0.2–0.4 | 0.2–0.4 | 0.2–0.4 | 0.2–0.4 | 0.3–0.5 | 0.2–0.4 | 0.05–0.1 | 0.2–0.4 | 0.05–0.1 |
| Specific surface area ($m^2/g$) | 6.1 | 6.1 | 6.1 | 6.1 | 7.5 | 6.1 | 75.0 | 6.1 | 75.0 |
| Amount of supported metal (%) | Cu:2.5 | Cu:4.8 | Cu:4.1 Zn:1.0 | Cu:5.0 | Cu:4.7 | Cu:1.8 Zn:1.9 | Cu:4.8 | Cu:4.6 | Cu:4.3 |

TEST EXAMPLE

The antimicrobial powders $A_2$, $A_5$, $A_6$, $A_7$, $A_8$ and $A_9$ obtained in Examples 2, 5, 6, 7, 8 and 9 were subjected to antimicrobial test using titanium dioxide $A_0$ supporting no antimicrobial metal on the surface of particles as a blank sample (which corresponds to the case of amount of antimicrobial metal being 0 in Tables 3–8).

Kind of microorganisms used for test were 10 kinds, namely, four kinds of bacteria: *Bacillus subtilis.* PCI 219, *Staphylococcus aureus* 209P, *Escherichia coli,* and i Pseudomonas aeruginosa and 6 kinds of molds and yeasts: *Trichophyton mentagraphytes, Trichophyton rubrum, Candida albicans, Penicillium citrinum, Aspergillus niger* and *Cladosporium herbarum.*

Test method was as follows: For bacteria, a given amount of antimicrobial powders were added to 10 ml of a bouillon-agar medium dissolved with heating and then the mixture was fully stirred by a test tube mixer to suspend the powders in the agar and then the suspension was poured into a petri disk of 9 cm in diameter and coagulated. Test microorganisms previously liquid cultured were coated on the surface of the agar and. The cultured at 37° C. for 18 hours and effect was evaluated according to degree of growth on the agar. For molds and yeasts, a given amount of antimicrobial powders were added to 10 ml of Sabouraudagar medium and in the same manner as for bacteria. This was poured into a petri dish and test microorganisms were coated thereon and cultured at 28° C. for 6 days and effect was evaluated. The results are shown in Tables 3–8. In these tables, "+" means that the powders had antimicrobial effect and "−" means that they had no antimicrobial effect.

TABLE 3

| Test microorganism | Antimicrobial powders $A_2$ addition amount (% based on medium) 0 | 0.5 | 1.0 | 2.0 | 5.0 |
|---|---|---|---|---|---|
| *B. subtilis* PCI 219 | − | + | + | + | + |
| *St. aureus* 209P | − | + | + | + | + |
| *E. coli* | − | − | + | + | + |
| *Ps. aeruginosa* | − | − | + | + | + |
| *Tr. mentagraphyres* | − | − | + | + | + |
| *Tr. rubrum* | − | + | + | + | + |
| *C. albicans* | − | + | + | + | + |
| *Pe. citrinum* | − | + | + | + | + |
| *As. niger* | − | − | + | + | + |
| *Cl. herbarum* | − | + | + | + | + |

TABLE 4

| Test microorganism | Antimicrobial powders $A_5$ addition amount (% based on medium) 0 | 0.5 | 1.0 | 2.0 | 5.0 |
|---|---|---|---|---|---|
| *B. subtilis* PCI 219 | − | − | − | − | + |
| *St. aureus* 209P | − | − | − | + | + |
| *E. coli* | − | − | − | − | − |
| *Ps. aeruginosa* | − | − | − | − | − |
| *Tr. mentagraphyres* | − | − | − | − | + |
| *Tr. rubrum* | − | − | − | − | + |
| *C. albicans* | − | − | − | − | + |
| *Pe. citrinum* | − | − | − | − | + |
| *As. niger* | − | − | − | − | − |
| *Cl. herbarum* | − | − | − | − | + |

TABLE 5

| Test microorganism | Antimicrobial powders $A_6$ addition amount (% based on medium) 0 | 0.5 | 1.0 | 2.0 | 5.0 |
|---|---|---|---|---|---|
| *B. subtilis* PCI 219 | − | + | + | + | + |
| *St. aureus* 209P | − | − | + | + | + |
| *E. coli* | − | − | − | + | + |
| *Ps. aeruginosa* | − | − | − | − | + |
| *Tr. mentagraphyres* | − | − | − | − | + |
| *Tr. rubrum* | − | − | − | − | + |
| *C. albicans* | − | − | − | − | + |
| *Pe. citrinum* | − | − | − | − | + |
| *As. niger* | − | − | − | − | + |
| *Cl. herbarum* | − | − | − | − | + |

TABLE 6

| Test microorganism | Antimicrobial powders $A_7$ addition amount (% based on medium) 0 | 0.5 | 1.0 | 2.0 | 5.0 |
|---|---|---|---|---|---|
| *B. subtilis* PCI 219 | − | + | + | + | + |
| *St. aureus* 209P | − | + | + | + | + |
| *E. coli* | − | + | + | + | + |
| *Ps. aeruginosa* | − | + | + | + | + |
| *Tr. mentagraphyres* | − | + | + | + | + |
| *Tr. rubrum* | − | + | + | + | + |
| *C. albicans* | − | + | + | + | + |
| *Pe. citrinum* | − | + | + | + | + |
| *As. niger* | − | + | + | + | + |
| *Cl. herbarum* | − | + | + | + | + |

TABLE 7

| Test microorganism | Antimicrobial powders $A_8$ addition amount (% based on medium) 0 | 0.5 | 1.0 | 2.0 | 5.0 |
|---|---|---|---|---|---|
| *B. subtilis* PCI 219 | − | − | − | + | + |
| *St. aureus* 209P | − | − | − | + | + |
| *E. coli* | − | − | − | − | − |
| *Ps. aeruginosa* | − | − | − | − | − |
| *Tr. mentagraphyres* | − | − | − | − | + |
| *Tr. rubrum* | − | − | − | − | + |
| *C. albicans* | − | − | − | − | + |
| *Pe. citrinum* | − | − | − | − | + |
| *As. niger* | − | − | − | − | + |
| *Cl. herbarum* | − | − | − | + | + |

TABLE 8

| Test microorganism | Antimicrobial powders $A_9$ addition amount (% based on medium) 0 | 0.5 | 1.0 | 2.0 | 5.0 |
|---|---|---|---|---|---|
| *B. subtilis* PCI 219 | – | – | – | + | + |
| *St. aureus* 209P | – | – | – | + | + |
| *E. coli* | – | – | – | – | + |
| *Ps. aeruginosa* | – | – | – | – | – |
| *Tr. mentagraphyres* | – | – | – | + | + |
| *Tr. rubrum* | – | – | – | – | + |
| *C. albicans* | – | – | – | – | + |
| *Pe. citrinum* | – | – | – | – | – |
| *As. niger* | – | – | – | – | – |
| *Cl. herbarum* | – | – | – | – | + |

REFERENTIAL EXAMPLE 1

To 10 g of one kind ($A_3$) of antimicrobial powders shown in Table 2 was added 10 ml of toluene. After sufficient stirring, thereto was added 4 g of acrylic resin (ACRYDICK manufactured by Dainippon Ink & Chemicals Inc.), followed by further stirring and mixing. All of this mixture was charged in a paint shaker manufactured by Red Devils Co. (internal volume: 90 $cm^3$ and filled with 40 g of glass beads of 1.0 mm in diameter) and mixed and dispersed by vertical motion for 30 minutes. The mixture was allowed to pass through a mesh to remove glass beads to obtain the following coating composition.

| Properties of coating composition | |
|---|---|
| PVC (Volume content of pigment) | 67% |
| SVC (Volume content of solid) | 25% |
| Viscosity | 250 c.p. |

This coating composition was hand coated on a polypropylene synthetic paper (about 100 μm thick: YUPO manufactured by Oji Yuka Co.) by a doctor blade (depth 50 μm). This was allowed to dry to the touch and left to stand overnight at 80° C. and then cut out into a circle (23 mm in diameter) to obtain a coated shaped product ($B_3$) of about 14 μm in dry film thickness and about 113 μm in total thickness.

REFERENTIAL EXAMPLE 2

10 grams of antimicrobial powders ($A_5$) shown in Table 2 were treated in the same manner as in Referential Example 1 to obtain a coated shaped product ($B_5$) of about 12 μm in coating thickness and about 115 μm in total thickness.

REFERENTIAL EXAMPLE 3

To 20 g of antimicrobial powders ($A_3$) shown in Table 2 was added 1 g of ethyl cellulose, followed by sufficient stirring. Then, 1 g of the mixture was charged in a concentric cylindrical mortar (having super hard alloy lining; inner diameter: 23 mm and outer diameter: 115 mm in diameter manufactured by Kikusui Seisakusho Co.) and subjected to hydraulic pressing by means of a columnar pestle (manufactured by Kikusui Seisakusho Co.; outer diameter: 23 mm).

Pressing procedure was as follows: Pressure was increased at 50 $kgG/cm^2$ per 1 minute and whenever the increment of pressure reached 400 kgG/cm2, the pressure at this time was kept for 10 minutes and then hydraulic pressure was released. Subsequently, the mortar was transferred onto a stair tread and hydraulic pressure was again applied to gradually press down the pestle to draw out the sample from the bottom of the mortar. In this way, a compression shaped product ($C_3$) with an outer diameter of 23 mm and a thickness of 1.0 mm was obtained.

REFERENTIAL EXAMPLE 4

Using 20 g of antimicrobial powders ($A_5$) shown in Table 2, a compression shaped product ($C_5$) with an outer diameter of 23 mm and a thickness of 1.1 mm was obtained in the same manner as in Referential Example 4.

REFERENTIAL TEST EXAMPLE

Antimicrobial tests were conducted using the antimicrobial shaped products ($B_3$, $B_5$, $C_3$ and $C_5$) obtained in Referential Examples 1–4 as test samples and coated shaped product ($B_0$) and compression shaped product ($C_0$) prepared by treating titanium dioxide supporting no antimicrobial metal on the surface (substrate particles in Table 1) in the same manner as in Referential Example 1 and 3, as blank samples.

Three kinds of bacteria, namely, *Staphylococcus aureus, Salmonella enteritidis* and *Escherichia coli* were used for the tests. The testing method was as follows: One or two of each sample were put in a petri dish containing 100 ml of sterilized physiological saline to which 0.10% of peptone was added (in case of two samples were used, these were put side by side). Then, thereon were inoculated a given amount of the bacteria and the antimicrobial activity of each sample was evaluated by counting the number of bacteria every 4 hours at a culturing temperature of 35° C. relative to the number of bacteria just after inoculation. The results are shown in Table 9 (in case of using one sample) and Table 10 (in case of using two samples).

TABLE 9

| Sample mark | Number of sample introduced | Bacteria | Number of bacteria just after inoculation | After 4 hours | After 8 hours | After 12 hours | After 24 hours |
|---|---|---|---|---|---|---|---|
| $B_0$ | 1 | *S. aureus* | 7900 | 16600 | — | — | — |
| | | *S. enteritidis* | 7100 | 12800 | — | — | — |
| | | *E. coil* | 8700 | 14800 | — | — | — |
| $B_3$ | 1 | *S. aureus* | 5700 | 4.0 | 0 | 0 | 0 |
| | | *S. enteritidis* | 7800 | 2300 | 1200 | 57 | 0 |
| | | *E. coil* | 7700 | 2200 | 1200 | 51 | 0 |
| $B_5$ | 1 | *S. aureus* | 8000 | 4.1 | 0 | 0 | 0 |
| | | *S. enteritidis* | 5300 | 1600 | 830 | 400 | 0 |
| | | *E. coil* | 5200 | 1500 | 790 | 380 | 0 |
| $C_0$ | 1 | *S. aureus* | 8500 | 18700 | — | — | — |
| | | *S. enteritidis* | 7200 | 13700 | — | — | — |
| | | *E. coil* | 8300 | 14900 | — | — | — |
| $C_3$ | 1 | *S. aureus* | 4900 | 7 | 0 | 0 | 0 |

TABLE 9-continued

| Sample mark | Number of sample introduced | Bacteria | Number of bacteria just after inoculation | After 4 hours | After 8 hours | After 12 hours | After 24 hours |
|---|---|---|---|---|---|---|---|
| | | *S. enteritidis* | 8200 | 5000 | 2700 | 1200 | 0 |
| | | *E. coil* | 5600 | 3400 | 1800 | 820 | 0 |
| $C_5$ | 1 | *S. aureus* | 8700 | 9.0 | 0 | 0 | 0 |
| | | *S. enteritidis* | 4800 | 2900 | 1500 | 720 | 0 |
| | | *E. coil* | 8900 | 5300 | 2700 | 1300 | 0 |

Note:
"—" means that counting was not effected.

TABLE 10

| Sample mark | Number of sample introduced | Bacteria | Number of bacteria just after inoculation | After 4 hours | After 8 hours |
|---|---|---|---|---|---|
| $B_0$ | 2 | *S. aureus* | 5100 | 10100 | — |
| | | *S. enteritidis* | 8400 | 14300 | — |
| | | *E. coil* | 5800 | 9300 | — |
| $B_3$ | 2 | *S. aureus* | 5600 | 0 | 0 |
| | | *S. enteritidis* | 6400 | 0.5 | 0 |
| | | *E. coil* | 8200 | 0.5 | 0 |
| $B_5$ | 2 | *S. aureus* | 6900 | 0 | 0 |
| | | *S. enteritidis* | 9200 | 8.1 | 0 |
| | | *E. coil* | 5100 | 4.0 | 0 |
| $C_0$ | 2 | *S. aureus* | 6700 | 12700 | — |
| | | *S. enteritidis* | 5900 | 8900 | — |
| | | *E. coil* | 8500 | 11900 | — |

TABLE 10-continued

| Sample mark | Number of sample introduced | Bacteria | Number of bacteria just after inoculation | After 4 hours | After 8 hours |
|---|---|---|---|---|---|
| $C_3$ | 2 | *S. aureus* | 6200 | 0 | 0 |
| | | *S. enteritidis* | 8600 | 13 | 0 |
| | | *E. coil* | 7500 | 11 | 0 |
| $C_5$ | 2 | *S. aureus* | 6400 | 0 | 0 |
| | | *S. enteritidis* | 5500 | 10 | 0 |
| | | *E. coil* | 5600 | 9.5 | 0 |

Note:
"—" means that counting was not effected.

What is claimed is:

1. A method for producing antimicrobial powders, which comprises compression mixing at least one antimicrobial metal selected from the group consisting of copper, zinc and alloys thereof with hydrous titanium oxide or titanium oxide particles to support the antimicrobial metal on the surface of the particles.

* * * * *